(12) United States Patent
Lepage et al.

(10) Patent No.: US 8,700,342 B2
(45) Date of Patent: Apr. 15, 2014

(54) MULTI-FREQUENCY BOND TESTING

(75) Inventors: Benoit Lepage, Québec (CA); Jason Habermehl, Stoneham (CA)

(73) Assignee: Olympus NDT Inc., Waltham, MA (US)

( * ) Notice: Subject to any disclaimer, the term of this patent is extended or adjusted under 35 U.S.C. 154(b) by 516 days.

(21) Appl. No.: 12/620,756

(22) Filed: Nov. 18, 2009

(65) Prior Publication Data

US 2011/0118991 A1    May 19, 2011

(51) Int. Cl.
- *G01B 5/28* (2006.01)
- *G01B 17/02* (2006.01)
- *G01N 19/04* (2006.01)

(52) U.S. Cl.
USPC ............. 702/35; 702/34; 702/39; 702/189; 73/150 A

(58) Field of Classification Search
USPC .................. 702/34, 35, 39, 189; 73/105 A
See application file for complete search history.

(56) References Cited

U.S. PATENT DOCUMENTS

2009/0150094 A1 * 6/2009 Van Velsor et al. ............. 702/39
2009/0168074 A1 * 7/2009 Monchalin et al. ............ 356/502

OTHER PUBLICATIONS

Olympus BondMaster 1000e+ product brochure and NDT.net Olympus BondMaster1000e+ product announcement dated Aug. 2007.*

* cited by examiner

*Primary Examiner* — Sujoy Kundu
*Assistant Examiner* — L. Anderson
(74) *Attorney, Agent, or Firm* — Ostrolenk Faber LLP

(57) ABSTRACT

A multi-frequency bond-testing system using acoustic probes in conjunction with NDT/NDI inspection instruments. Bond-testing of test objects is carried out at multiple discrete frequencies to produce a single, combined amplitude C-scan. Alternatively, or in combination, the system provides a single, combined phase C-scan to enable proper interpretation of the C-scans. Amplitude and/or phase readings on test objects are normalized at the selected frequencies relative to tests performed on a defect-free object at those frequencies. In this manner, the non-linear behavior of a bond-testing probe over a frequency range chosen for a given inspection is compensated for. The invention enables providing more easily interpretable and sharper images which enable a more reliable and faster reading and identification of defects in the test objects.

18 Claims, 11 Drawing Sheets

MULTI-FREQUENCY BOND TESTING

FIELD OF THE INVENTION

The present invention relates to non-destructive testing and inspection systems (NDT/NDI) and more particularly to a multi-frequency bond testing system using acoustic probes in conjunction with NDT/NDI inspection instruments.

BACKGROUND OF THE INVENTION

Bond-testing (BT) equipment, such as the ONDT Bondmaster1000e+ using pitch-catch probes, offer a method for one sided non-destructive inspection of honeycomb sandwich composite materials. The pitch-catch (P-C) probe generates acoustic waves in the part using a first tip pressed in contact with the surface, and reads vibrations using a second tip simultaneously in contact with the surface. The probe can then detect defects through changes in vibration amplitudes and/or changes in propagation delays (phase) from generating tip to receiving tip.

The detection capability of a given pitch-catch (P-C) bond-testing (BT) non-destructive instrument is directly related to the nature and size of a given defect and the frequency used to detect the defect. Composite honeycomb sandwich structures can present various types of defects ranging from skin to core disbond or crushed core (disbond) and skin to skin disbond (delamination). A typical repair artifact referred to as potting can also be detected with the P-C technique. The relation between the detection capability and the relation between the defect size and test frequency is notable for small defects which are detected at a limited range of resonant frequencies. Large defects can typically be detected over a larger range of test frequencies.

Disbond type indications are typically detected by an increase in signal amplitude for a given frequency. Delamination and potting type indications are quite different in that the amplitude for such indications remains relatively stable; however, the phase of the return signal varies due to the effect on the acoustic wave speed caused by these indications. Delamination type defects lead to a decreased wave speed whereas potting type defects lead to an increased wave speed. As the optimal test frequency depends on the test part structure (i.e. number of plies, ply type, core thickness, core type) and on the defect type, shape and size, selection of a single frequency for inspection can be troublesome.

Yet another drawback of the background art is its inability to distinguish between various defect sizes. In fact, there are some test situations when a smaller defect can generate a stronger signal than a bigger defect at a given frequency.

To ensure a good possibility of detection (POD) for a range of defect sizes including small defects during a BT inspection, several frequencies must be used. These test frequencies should fully cover the frequency range over which real defects are likely to occur in a given sample.

To provide inspection data for multiple inspection frequencies, most background art units offer a "sweep" inspection mode which sequentially alternates through a band of excitation frequencies. However, data acquisition goes through a single set of test parameters (gain, phase angle, etc) to be displayed in a unique impedance plane. This method has important limitations resulting from the non-linear probe response over its operating frequency range. As presented in FIG. 3, the probe response over a good portion of a test sample varies over the frequency range. There is therefore an inherent disadvantage to using the same inspection settings for all test frequencies and displaying the results from all test frequencies in the same impedance plane. Detection of phase shift using the "sweep" mode is also nearly impossible.

Another disadvantage with the background art is that few systems offer a means for representing BT data in a C-scan. Most currently available systems provide manual inspections but cannot provide a two-dimensional mapping of the test sample. Although representing impedance plane data into a readily interpretable C-scan image is provided by the background art for a limited range of frequencies, means for combining data from a relatively large range of multiple frequency C-scans into a combined C-scan without negatively affecting POD and signal-to-noise ratio (SNR) is not known to be an available solution.

Considering the aforementioned drawbacks and disadvantages, there is a great need for a multi-frequency bond testing instrument with a data representation and test method having the ability to meet the following objectives: a) represent the BT amplitude at multiple test frequencies on a single C-scan image; b) compensate the non-linear behavior of the BT probe over the frequency range; c) differentiate defects of various sizes, improve or at least maintain the signal-to-noise ratio observed when scanning at specific frequencies; and d) detect delamination type defects and differentiate similar signals originating from potting.

SUMMARY OF THE INVENTION

The invention disclosed herein aims to solve the problems related to bond testing non-destructive testing. More specifically, the invention aims to provide a method of testing a material sample for defects, comprising the steps of applying a test signal to the material sample, receiving a return signal from the material sample and analyzing the return signal to determine whether the material sample is defective, wherein the steps of applying a test signal and receiving a return signal are repeated for signals at a plurality of discrete frequencies.

Furthermore, the invention provides a means for combining test signals from multiple frequencies into a single combined amplitude C-scan. The invention also provides a means for combining test signals from multiple frequencies into a single combined phase C-scan.

It is further an object of the present disclosure to make use of the advantages of combining the results from multiple test frequencies to provide a means for improving possibility of detection for a range of defect sizes and differentiating defects of various sizes.

Accordingly, it is a general object of the present disclosure to provide a means to compensate the non-linear behavior of the BT probe over the frequency range chosen for a given inspection. Specifically, it an object of the current invention to normalize the amplitude response of the return signals for each frequency.

It is further an object of the present invention to provide a means for selecting an appropriate frequency range for a bond testing inspection.

It is further an object of the present disclosure to make use of the phase of test signal responses to provide a means to detect and differentiate disbond type defects as well as delamination type defects and to differentiate similar signals originating from potting.

It is an object of the present invention to provide a means for compensating the phase responses from multiple frequencies when combining these responses into a combined C-scan.

It is further an object of the present disclosure to provide a means for combining amplitude and phase components of test signals at single and multiple frequencies into a single C-scan.

It is yet further another object of the present disclosure to provide a method for bond testing including acquiring reference data from a good test sample, acquiring defect signatures from known defects, providing a means for selecting the most appropriate test frequencies for a given inspection including generating appropriate displays, providing combined multiple frequency bond testing amplitude, phase and combined amplitude and phase C-scan displays of the signal responses.

It is further an object of the present disclosure to provide a software or firmware program to enable existing hardware to perform the above mentioned.

BRIEF DESCRIPTION OF THE DRAWINGS

Features and advantages of the present invention will become apparent from the following description of embodiments thereof, by way of example only, with reference to the accompanying drawings, in which.

DETAILED DESCRIPTION OF THE INVENTION

The invention is a novel method to acquire, represent, and display the amplitude and phase based results of a multi-frequency pitch-catch bond testing inspection. The invention also relates to a test method that simplifies the setup and uses of multi-frequency bond testing equipment.

Figure 1:
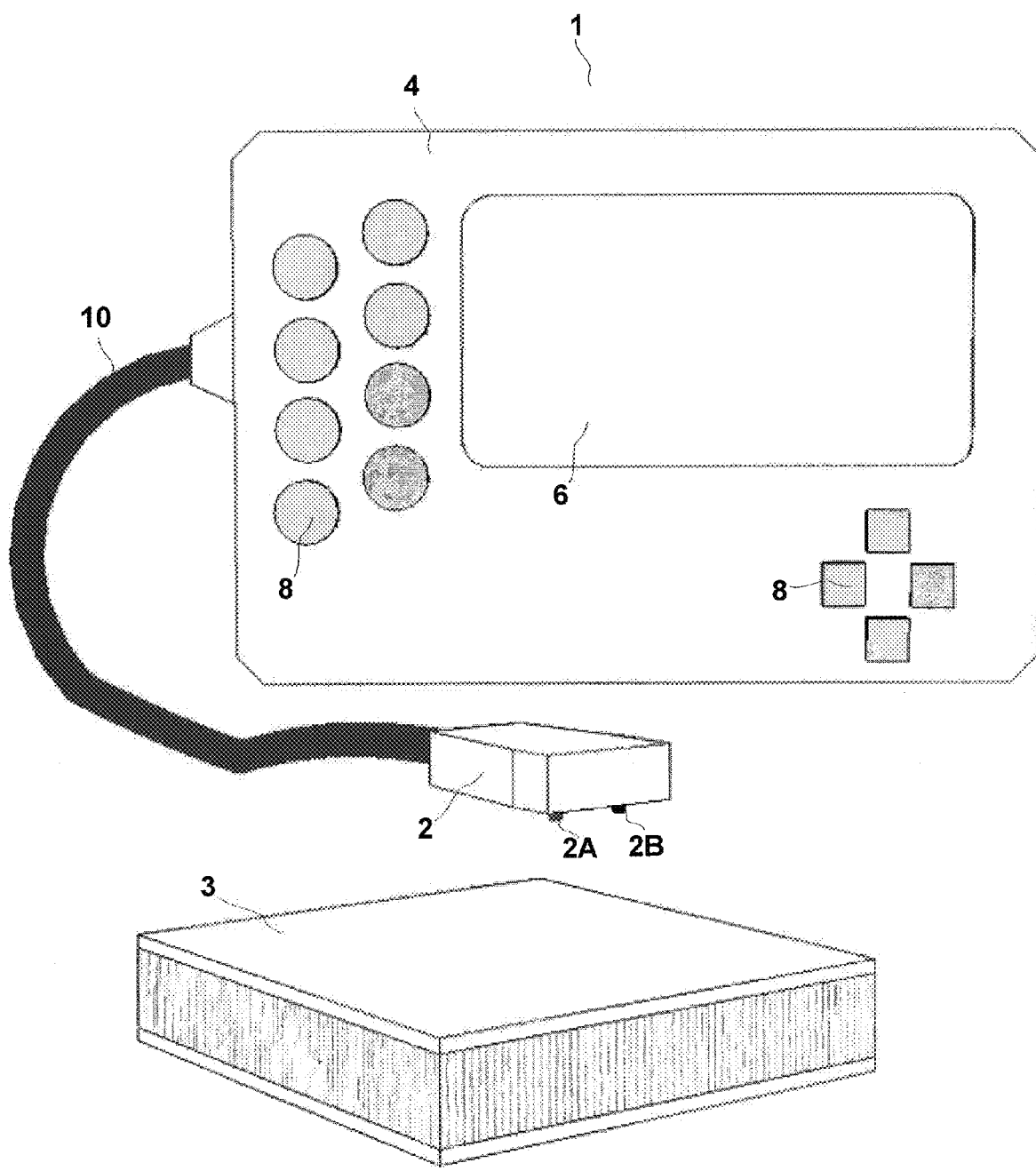
FIG. 1 is a diagram of an apparatus in accordance with an embodiment of the present invention.

Referring to FIG. 1, an apparatus in accordance with the present invention is illustrated. The apparatus 1, comprises a probe 2 for applying multiple test signals to a composite test sample 3 and for receiving return signals from the test sample 3. In this embodiment, the means of applying and receiving the test signals may comprise a conventional pitch-catch probe having two spring loaded contact tips 2A and 2B set apart a pre-determined distance, typically in the order of 10 mm, which in operation are held in contact with a test sample 3. One of these contact tips acts as the frequency driver, and is arranged to be driven with a test signal in the acoustic to low-ultrasonic frequency range. The second contact is arranged to receive the return signal, after the signal has passed through test sample 3.

Probe 2 is connected by cable 10 to means for driving the probe 2 at multiple frequencies and receiving and processing the return signals, which in this embodiment is a multi-channel acquisition and computing apparatus (ACU) 4. ACU 4 includes a display 6 and means for interfacing 8 with a user. Such means for interfacing can include buttons, knobs, dials, a mouse (not shown) and a keyboard (not shown).

It will be appreciated that sample 3 shown in FIG. 1 may be part of a larger item such as an aircraft e.g. a panel of an aircraft. Note that, practically, panels for items such as aircraft are tested in situ, so apparatus of FIG. 1 must be transportable to be able to be used to test an item in question. It will be appreciated that one (linear) or two dimensional (raster) scans are typically performed within the scope of this invention. The encoded scanning means can be a linear encoder, a two-axis scanner or others. The scanning means can be manual or automated.

In accordance with the present invention, acquisition and computing apparatus 4 is arranged to cause probe 2 to output multiple drive signals at discrete frequencies and receive the associated return signals in separate sequential time durations. In the preferred embodiment, apparatus 1 allows for information from separate frequencies and/or separate probe configurations to be treated as independent channels. More specifically, all channels use the same single physical input for the required duration (each pulse being typically 5 to 7 cycles long). Each of these time durations is referred to herein as a 'time-slot'.

Figure 2:
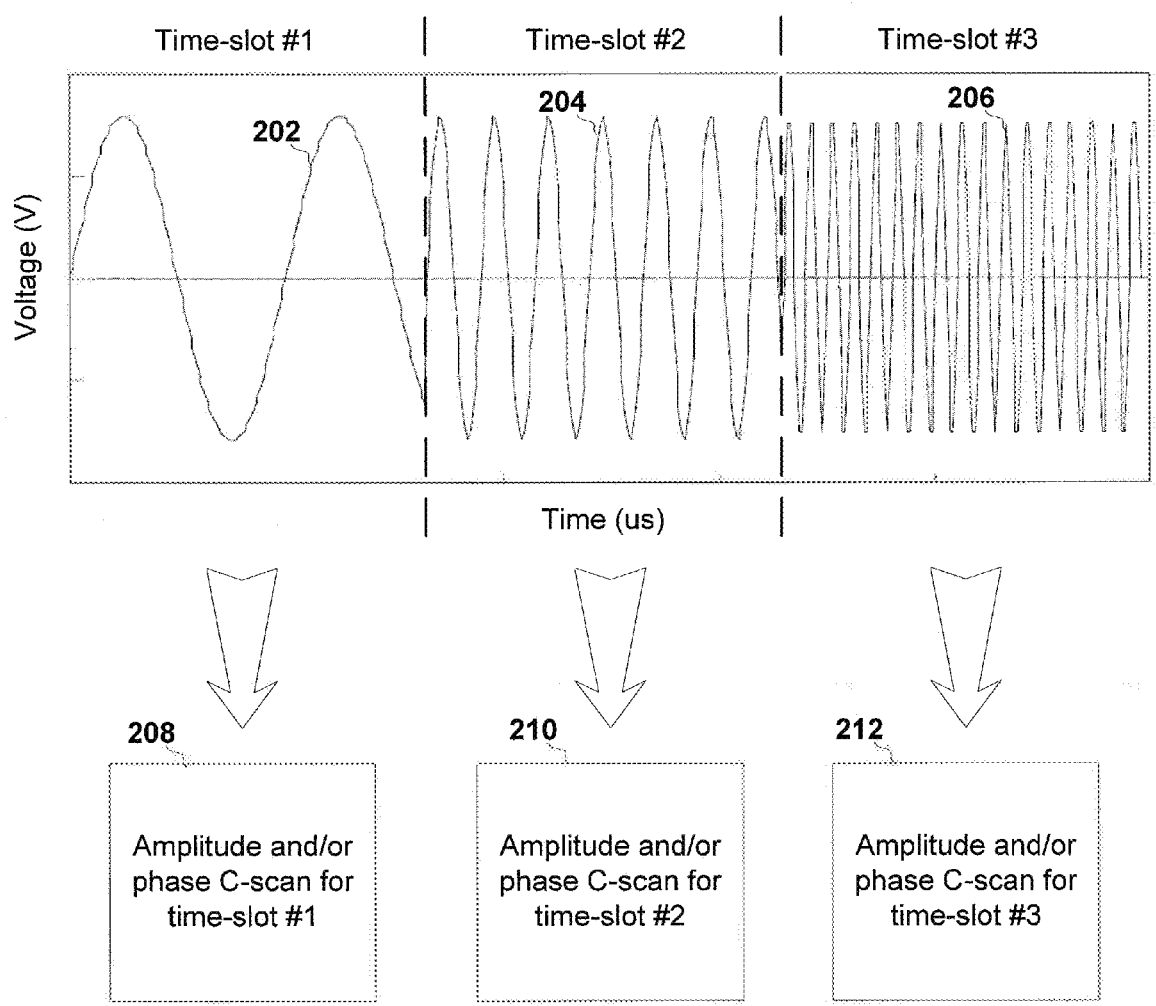
FIG. 2 is a representation of three exemplary discrete frequency time slots employed for the measurement method of the present invention.

Referring to FIG. 2, a representation of three exemplary BT channels is shown. Each time-slot is associated with a different frequency signal 202, 204, 206 for time-slots #1, #2 and #3 respectively. For a given channel associated with a given time-slot, emission and reception frequencies are discrete and the same. Each channel can be thought of as a completely separate and independent inspection, each channel being multiplexed to acquire data associated to a given discrete frequency. The data from each channel is indexed and stored separately.

A complete acquisition cycle is defined as the process to sequentially go through all of defined time-slots. In the preferred embodiment, each time-slot and its associated discrete drive frequency will be henceforth referred to as a 'discrete frequency time-slot' or 'DFTS'. In accordance with the present invention, a C-scan display of amplitude and phase can be provided separately for each acquired channel as depicted by 208, 210 and 212 in FIG. 2.

First Aspect of the Invention: Combined Multi-frequency Amplitude Display

In accordance with the present invention, the return signals from multiple time-slots can be combined to more readily provide an easily interpretable combined C-scan display.

Also in accordance with the present invention, a means and method for selecting appropriate drive frequencies for a given inspection is provided.

Figure 3:
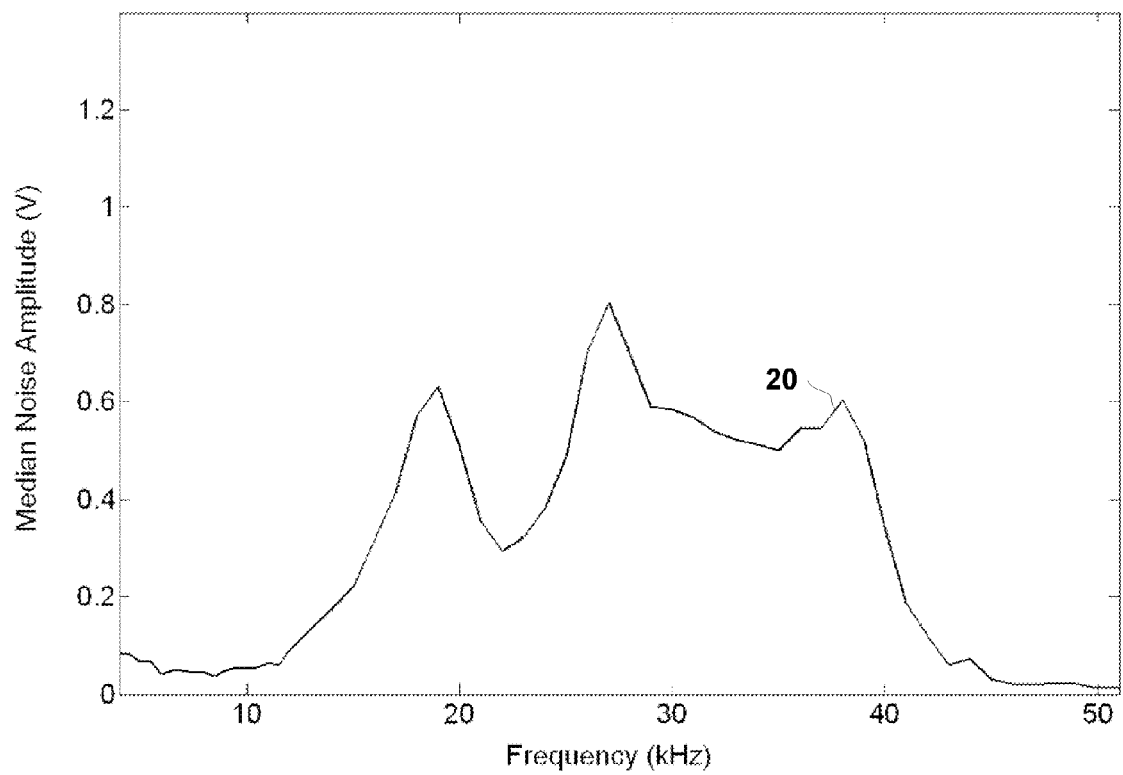
FIG. 3 is a representation of a response (signal amplitude versus frequency) of a typical BT NDT signal over a range of frequencies from a fixed position on a good portion of a test sample.

Referring to FIG. 3, curve 20 provides an amplitude data transfer function between the driver and receiver probe tips at multiple discrete excitation/reception frequencies from a fixed position on a good test sample—i.e. one without flaws. It is readily apparent that the amplitude response on a good test sample is dependant on the test frequency. This baseline amplitude response is herein referred to as 'Reference Amplitude' Using the reference amplitude response from a good test sample as a baseline, amplitude responses obtained during scanning of a test sample can be normalized by dividing the reference response at each given frequency with the signal response (raw amplitude) at the same frequency. This normalization is performed for all frequencies selected for a given inspection defined herein as the 'test frequency range'.

$$A_{norm}(x, y, f) = \frac{A_{raw}(x, y, f)}{A_{ref}(f)}$$

Where:
$A_{norm}$(x,y,f)=Normalized amplitude data at a given frequency (f) and scan position (x,y)
$A_{raw}$(x,y,f)=Raw Amplitude reading at a given frequency (f) and position (x,y)
$A_{ref}$(f)=Reference amplitude of the response at frequency (f)

Figure 4:
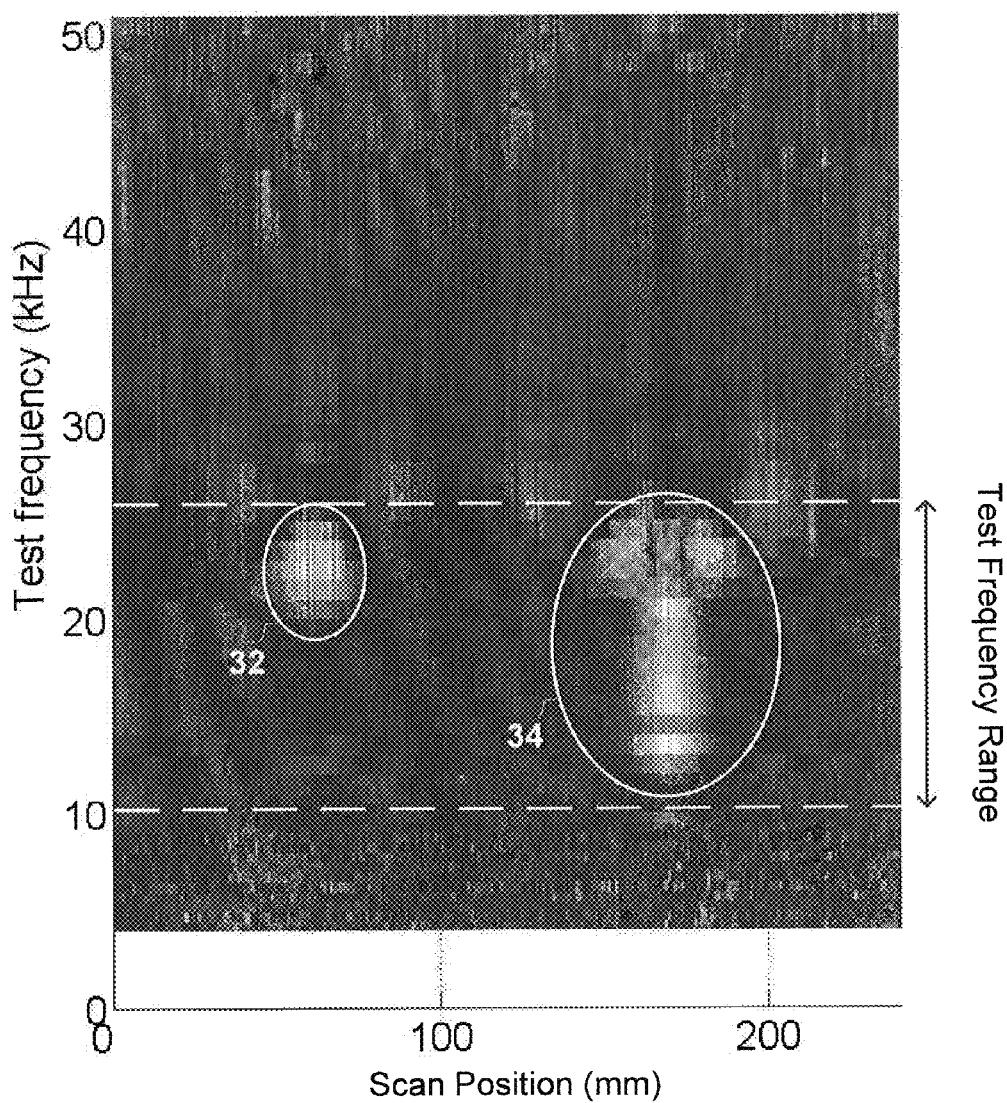
FIG. 4 is a representation of a response (normalized signal amplitude versus frequency and scan position) associated with a linear scan of a portion of a test sample having two known disbond defects of different sizes.

Prior to performing an inspection, it is advantageous to appropriately select the test frequency range that will be used for a given inspection. In this respect, normalized amplitude data from known defects can be obtained over a range of frequencies and presented as in FIG. 4. In this figure, a linear scan over two known 0.5" disbond diameter 32 and 1" disbond diameter 34 is displayed as a two-dimensional graphic with the X and Y axis representing scan position and frequency respectively. A linear color palette is used to represent the normalized amplitude for each frequency at each position. In the present example, a gray scale color palette is chosen with white showing maximum amplitude and black showing minimum amplitude. It is clear from this graphic that not all frequencies are required to adequately detect both of these disbonds. In fact, a reduced frequency range of between 10 and 25 kHz would be sufficient to cover all of the resonances from both of these disbonds. It is therefore apparent that the representation in FIG. 4 provides a means for readily determining adequate frequencies for detecting known defects typically present in calibration standards and such. Reducing the quantity of frequencies used for a given inspection provides for faster inspections without compromising POD or SNR. The quantity of frequencies may be provided by the user or other means.

Figure 5:
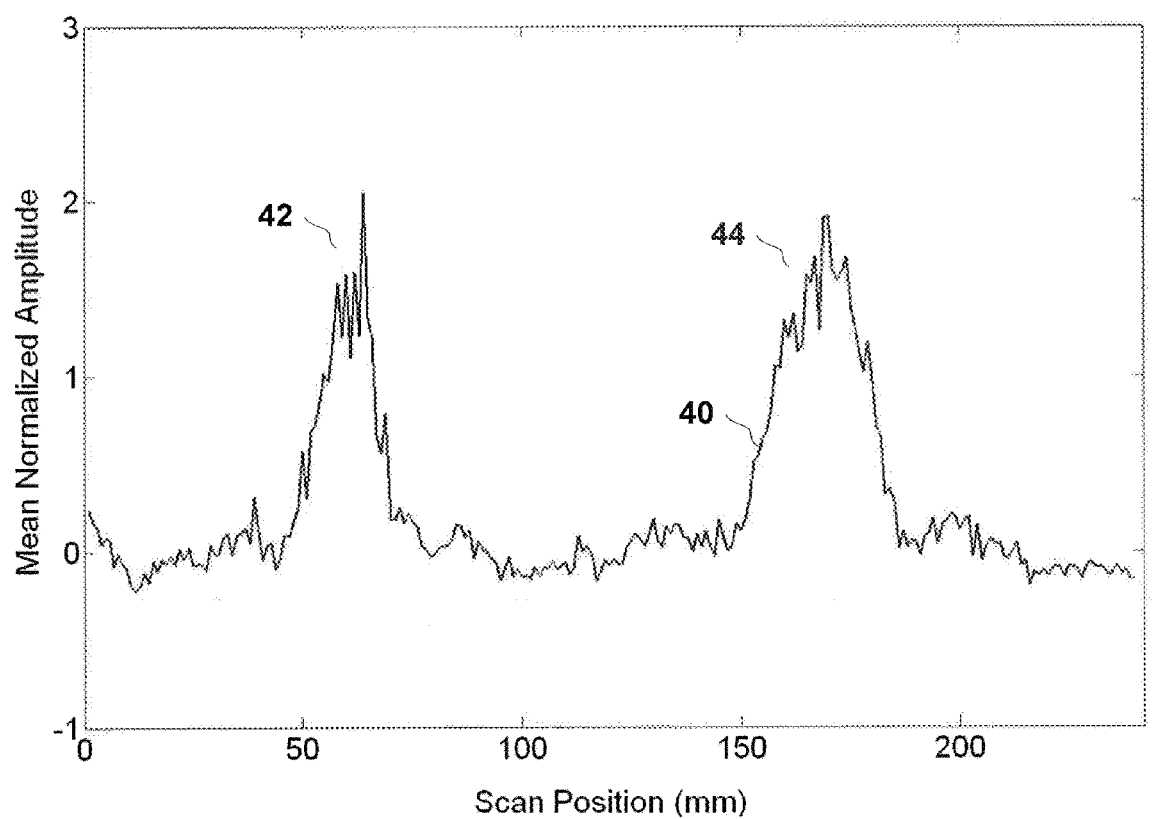
FIG. 5 is a representation of a response (combined signal amplitude versus scan position) associated with a linear scan of a portion of a test sample having two known disbond defects of different sizes.

From the chosen range of discrete frequency time-slots (DFTS's), multiple C-scans displaying return signal amplitudes for each DFTS can be displayed by inspection apparatus 1 (FIG. 1). Alternatively, in accordance with the present invention, a combined C-scan can be rendered from the multiple C-scans associated with each frequency in the chosen frequency range. This novel aspect provides a comprehensive and user friendly C-scan display. An average value of the normalized amplitude is also calculated for every position of the scan for the chosen range of DFTS's. The result of this process is a single amplitude value for each position of the scan with contributions from the return signals from all of the time-slots. FIG. 5 represents the mean normalized amplitude of the same one-line scan represented in FIG. 4. Data curve 40, including data 42 and 44 at different scan positions, is a representation of the combined amplitude for a one-line scan and is generated by calculating the mean normalized amplitude value from the selected frequency range for each position in the one-line scan as shown below.

$$A_{comb}(x, y) = \frac{\left( \sum_{f=min}^{max} \frac{A_{raw}(x, y, f)}{A_{ref}(f)} \right)}{Nb_f}$$

Figure 6:
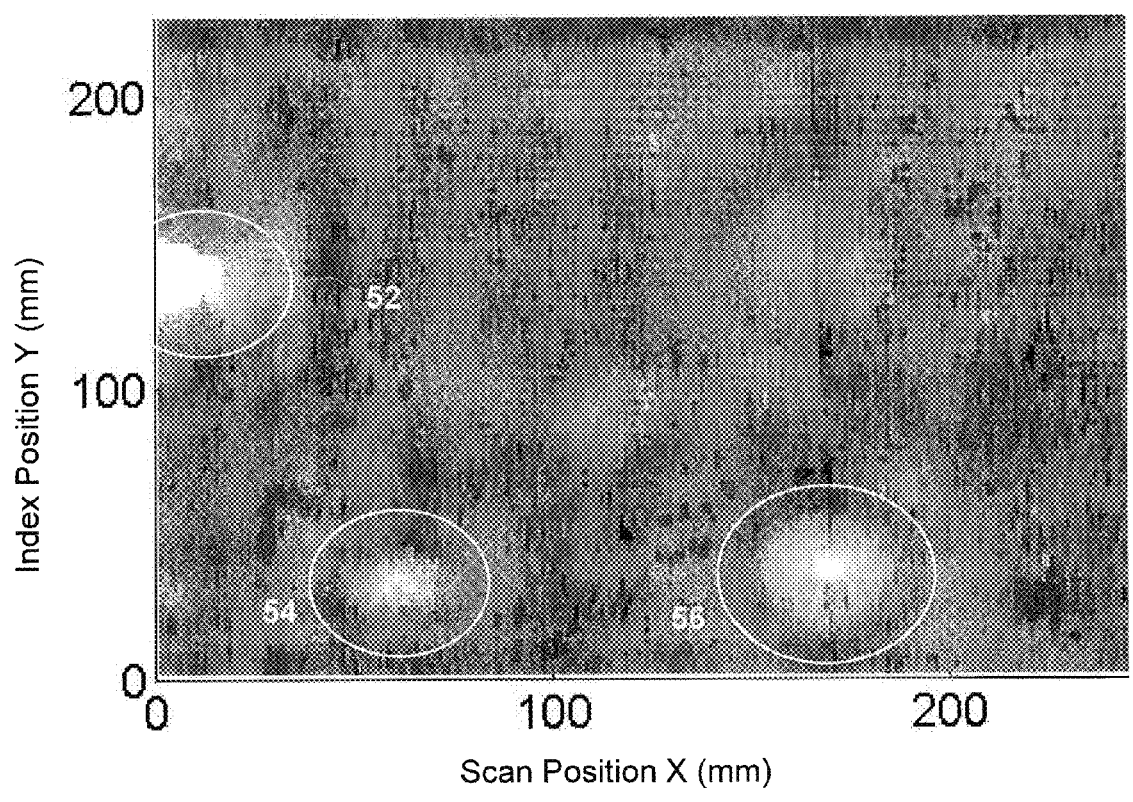
FIG. 6 is a representation of a response (signal amplitude versus scan position) associated with a raster scan of a portion of a test sample.

Where:
$A_{comb}$(x,y)=Combined amplitude data at a given scan position (x,y)
$A_{raw}$(x,y,f)=Raw Amplitude reading at a given frequency (f) and position (x,y)
$A_{ref}$(f)=Reference amplitude of the response at frequency (f)
$Nb_f$=Total number of test frequencies FIG. 6 illustrates a two-dimensional scan showing combined amplitudes represented by a grey scale color palette (C-scan). The C-scan clearly shows the presence of 0.5" diameter disbond 54, 1" diameter disbond 56 as well as a pull tab 52.

It will be appreciated by persons skilled in the art that 0.5" disbond 54 appears to be about half the size of 1" disbond 56. This is a noticeable effect and advantage of the multi-frequency embodiment as single discrete frequency C-scans only show one vibration mode for a given disbond which has the disadvantage of not accurately representing the actual physical shape or relative size of the defects. Combining the results from multiple frequencies provides a more accurate 'picture' of each disbond by simultaneously providing information for all of the vibration modes present within the chosen DFTS range. A substantially improved means for sizing defects is thereby provided by the present invention.

The combined amplitude of a larger defect detected over a large frequency range is therefore amplified by the combining process as compared to smaller defects. This is a highly desirable feature of the invention.

Second Aspect of the Invention: Phase Display

Multiple defect types can be present in typical sandwich type composite samples. Disbonds are the common cause of concern in these types of samples and can be readily detected using the amplitude based inspection methods described above. However, delamination type defects can also be present. Other indications such as potting can be present that are not considered to be actual defects but are the result of previous repair operations. Discrimination between a delamination and potting type indications from low signal-to-noise ratio disbonds can be difficult. It would therefore be advantageous to provide a method for adequately detecting delamination and potting type defects and for discriminating these defects from more potentially detrimental disbond defects.

Delamination and potting type indications are not readily detected with amplitude based inspection methods. These indications can however be detected with phase based inspection methods such as that presented herein. A separate process is required to monitor phase shift through the frequency range. Phase shift is caused by changes in wave speed. Wave speed is typically affected by the presence of a delamination (reduction of wave speed) or by the presence of potting material (increase of wave speed).

Figure 7:
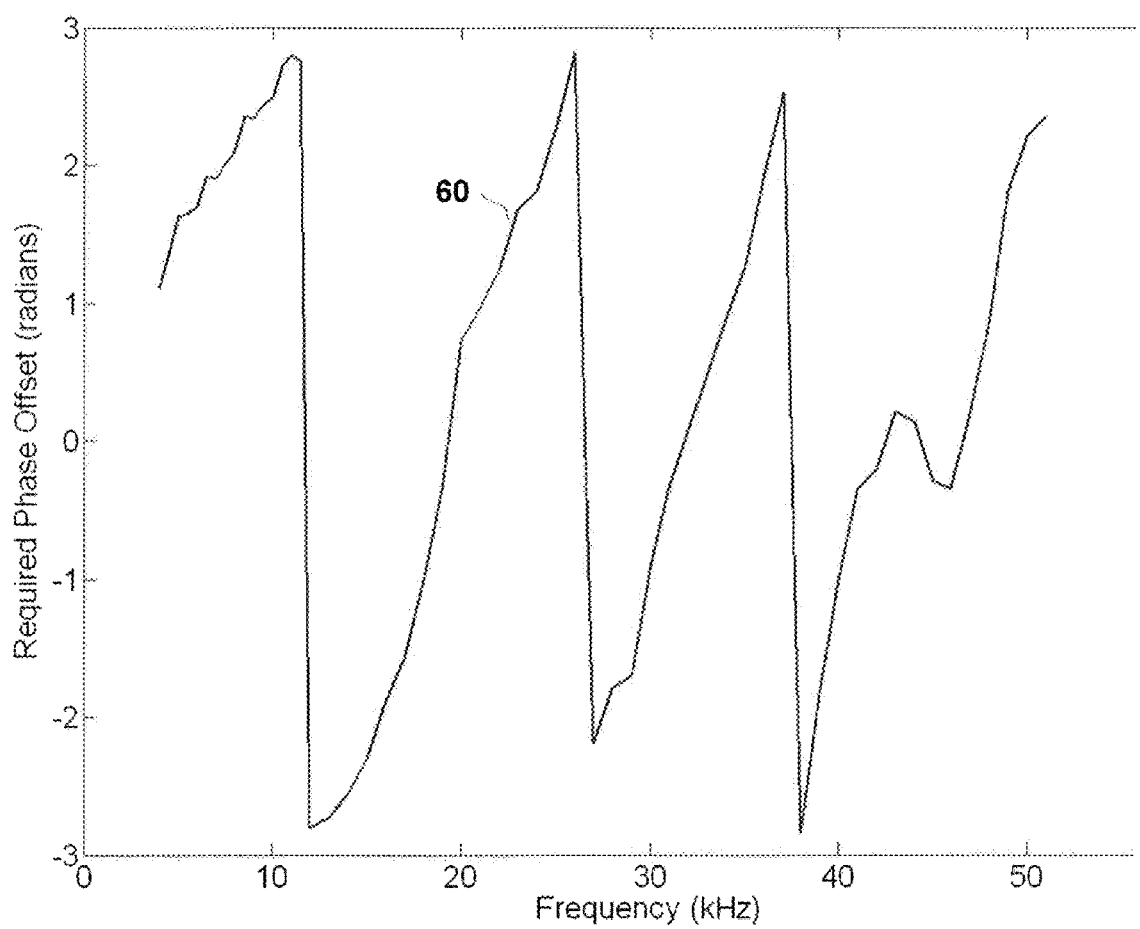
FIG. 7 is a representation of a response (signal phase versus frequency) of a typical BT NDT signal over a range of frequencies from a fixed position on a good portion of a test sample.

Referring to FIG. 7, a phase angle compensation curve is then built providing the phase offset from a defect-free test sample for each frequency within the frequency range. The phase compensation curve derived from a good part is in fact the phase lag between the sinusoidal signal sent through the driver tip 2A and received by reception tip 2B. The phase compensation curve represents the phase angle rotation required to set the signal vector at 0° phase angle in the impedance plane.

Figure 8:
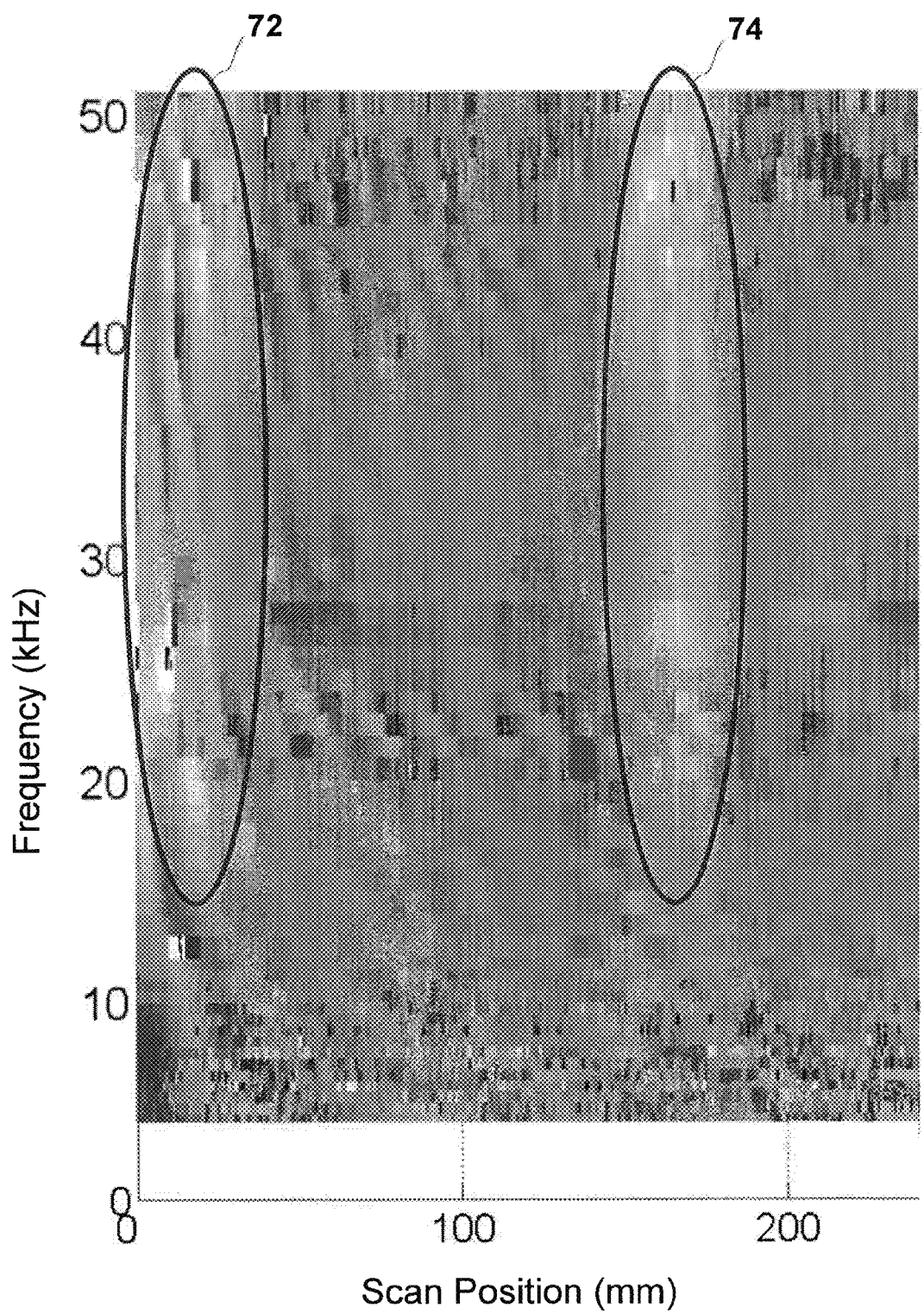
FIG. 8 is a representation of a response (signal phase lag versus frequency and scan position) associated with a linear scan of a portion of a test sample having two known defects of different sizes.

Referring to FIG. 8, the phase lag of the return signals compared to the phase measured on a good part at multiple frequencies can be plotted for a one-line scan that includes calibration defects. It should be noted that the phase lag shown has been compensated with the phase compensation curve 60 of FIG. 7. This phase plot of FIG. 8 includes the pull tab defect 72 and the 1" delamination defect 74. In the preferred embodiment the color palette (or gray scale) is such that a phase of +π is the same color (shade) as a phase of −π to remove potential discontinuities. An appropriate frequency range to achieve detection of the desired defect is readily available from the B-scan plot. Take note that the use of multiple frequencies increases the SNR by reducing the noise level as defects are detected over a broad frequency range. In the preferred embodiment, phase angle processing does not require normalization.

Figure 9:
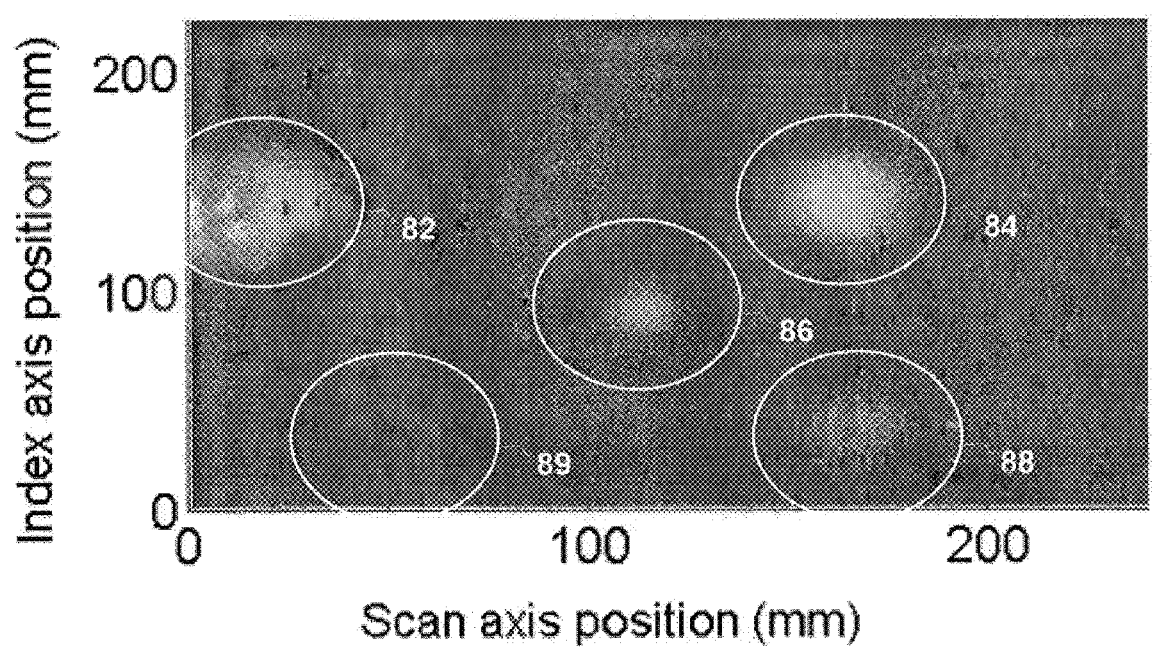
FIG. 9 is a representation of a response (signal phase versus scan position) associated with a raster scan of a portion of a test sample.

In accordance with the present invention, the phase of the return signals at multiple frequencies can be plotted in a C-scan display to provide information depicting the presence of delamination type defects and potting. Due to the opposite effect on acoustic wave propagation speed caused by problematic delamination type defects and non-problematic potting indications it is possible to discriminate between these two types of indications using phase shift information. In the preferred embodiment, the average phase shift over the chosen frequency range is used to generate the C-scan. Referring to FIG. 9, a C-scan display using the same test sample as used for FIG. 6 is shown. Note that the phase C-scan of FIG. 9 exhibits the improved detection of the 1" delamination defect 84 present in the sample. Note also that the detection of both disbonds 88 and 89 is significantly lower as compared to the amplitude C-scan in FIG. 6. Comparing the amplitude C-scans of FIG. 6 to phase lag C-scans of FIG. 9 therefore leads to a superior means for discriminating between disbond and delamination type of defects.

Figure 10:
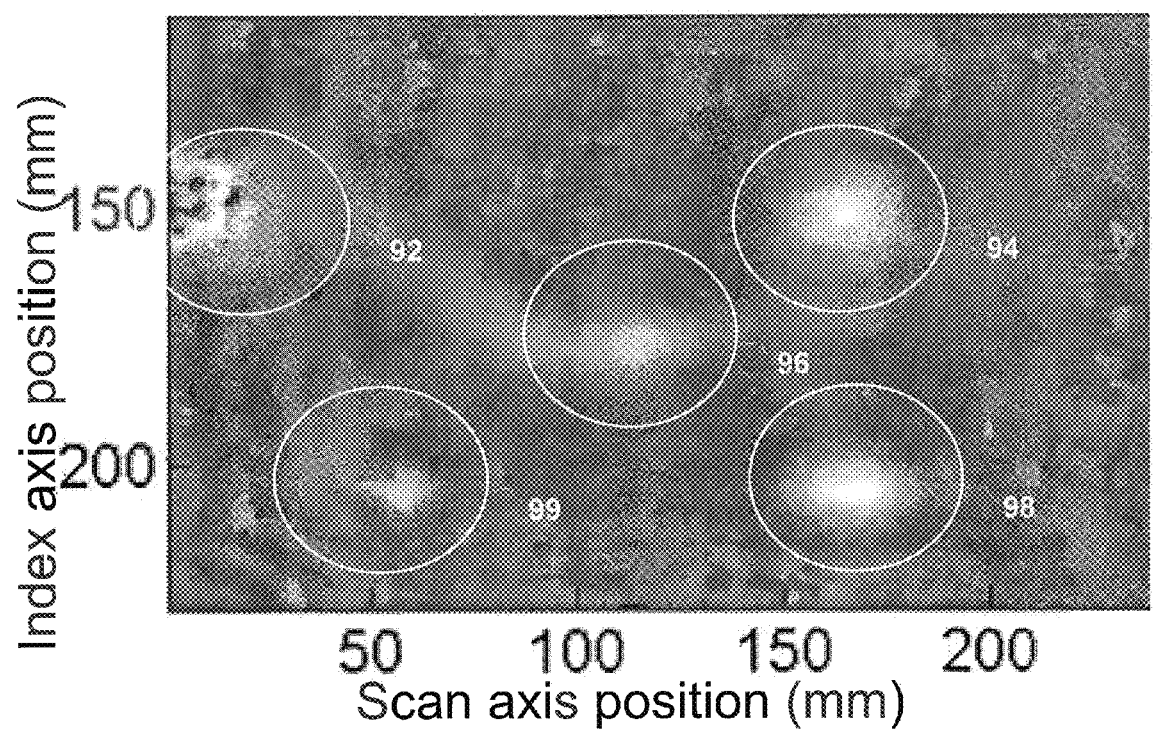
FIG. 10 is a representation of a response (combined amplitude (maximum) and phase versus scan position) associated with a raster scan of a portion of a test sample.

Referring to FIG. 10, in accordance with the present invention, a composite C-scan can be generated representing amplitude and phase data. In the preferred embodiment, a common scale for each separate C-scan is used and the individual amplitude and phase C-scans are generated by keeping the maximum value for the composite display. Alternatively, the amplitude and phase values can be summed to provide the composite C-scan display. This composite display presents a means for detecting all defects types in a single display. For example, FIG. 10 depicts disbond defects 98 and 99, pull tab defect 92, as well as delamination defects 94 and 96 in single display image. In the preferred embodiment, at least three displays are available to the user during an inspection, these being: 1) combined amplitude, 2) combined phase, and 3) composite amplitude and phase. Alternatively, additional displays can be made available such as the amplitude and phase C-scans associated to each frequency used for the inspection.

Note that FIG. 6 and FIG. 9 provide C-scans of the exact same test sample. Disbonds are clearly detected on the amplitude scan only while delaminations are clearly detected on phase scan only. The only defect detected on both scan is the pull tab delamination.

Test Method for Use of the Composite Amplitude and Phase Scans

Figure 11:
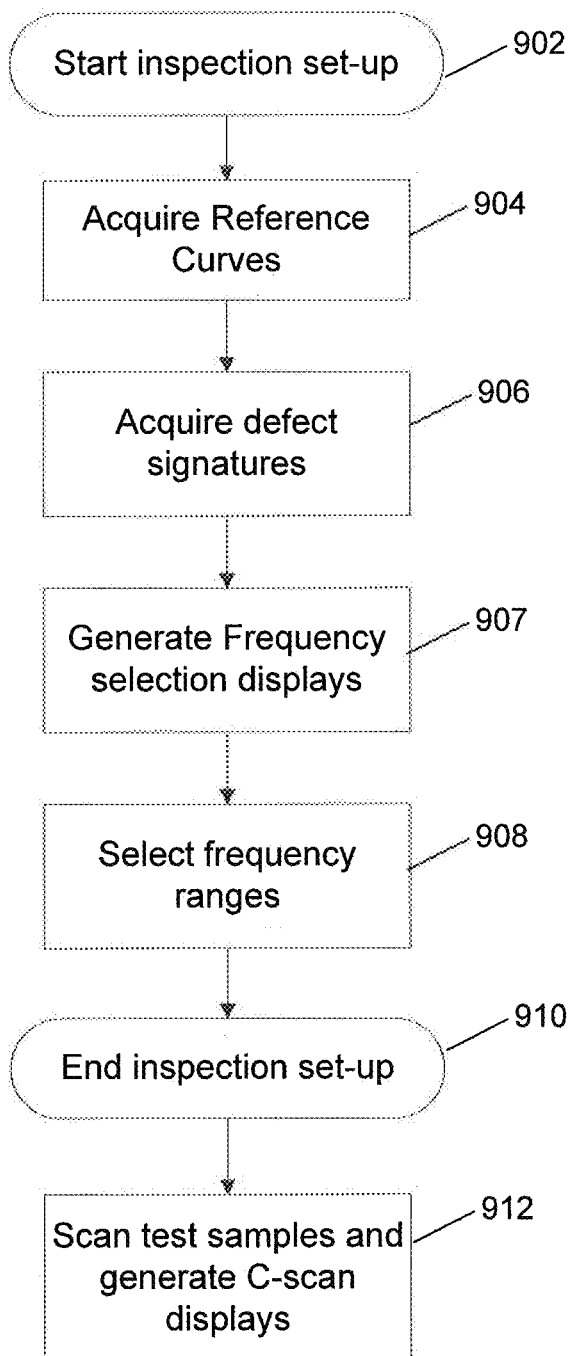
FIG. 11 is a flow chart describing the method of the preferred embodiment

The method for exploiting the multiple frequency bondtesting representation is described in FIG. 11. Prior to inspecting a given test sample, various parameters must be configured. At step 902 the inspection set-up is started. Initially, at step 904 the reference curves are acquired for both amplitude and phase data such as those presented in FIG. 3 and FIG. 7 using reference samples without flaws. In the preferred embodiment, the probe is placed on a good portion of a reference sample, or on a good portion of a test sample, and the signal amplitude versus frequency and signal phase versus frequency over a full range of DFTS's are acquired to constitute the amplitude 40 and phase 60 reference curves respectively. Alternatively, the signature signals from good portions of reference sample can be acquired using a linear scan.

The data from multiple defect free positions can be averaged to provide more constant reference curves. Using the reference curves acquired in step 904, subsequent amplitude data acquisitions are normalized by dividing the newly acquired data by the reference curve 20 (FIG. 3) and phase data acquisitions are compensated by subtracting the phase from the reference curve 60 (FIG. 7). Note that normalizing the amplitude response for each frequency can be performed during or after data acquisition.

In step 906 the probe is moved over known defects using the full range of DFTS's. In this step, the amplitude and phase signatures of the known defects are acquired. In the preferred embodiment, this step acquires the signatures from the smallest and largest disbonds requiring detection. Also, advantageously, this step acquires the signature of a delamination type defect. Alternatively, step 904 can be combined with step 906 whereby the amplitude and phase reference curves are generated by parsing the scanned acquisition data between the good and the known defective portion of the test sample. In step 907, the test frequency range is displayed as shown in FIG. 4 to indicate the frequency range where disbonds 32 and 34 appear, thereby allowing the instrument settings to be bandwidth limited to optimize the signal-to-noise ratio (SNR).

To provide adequate SNR or optimal scanning speed for the inspection of test samples, the number of DFTS's can be selected or limited for the inspection in step 908. Furthermore, discrete frequencies for each DFTS can also be selected in step 908, the range of which will depend on the signal response from reference samples with known defects for which detection of similar defects on a test sample is required. In step 912, after the end of inspection setup step 910, normalized signal amplitude versus frequency and scan position and compensated signal phase versus frequency and scan position scans are displayed (FIG. 4 and FIG. 8). From the amplitude and phase signal versus frequency and scan position displays, a frequency range can be chosen for amplitude and phase inspections respectively. In the preferred embodiment, the frequency range for amplitude and phase inspections can be different. Alternatively, the same range can be selected for both inspection types.

Once the frequency ranges have been selected in step 908, the inspection set-up is complete in step 910. In step 912, test samples can be inspected by scanning the probe over the test sample and generating C-scans displays as those presented in FIG. 6 and FIG. 9. On these C-scan displays, various defects types are readily detected by variations in amplitude and/or phase.

In the preferred embodiment, combined amplitude and combined phase C-scans are displayed separately. Advantageously, the preferred embodiment provides an additional composite C-scan display of both amplitude and phase data thereby representing all defect types on a single display.

Alternatively, prior to step 904, a choice may be made as to whether amplitude, phase or both inspection types are to be configured during the inspection set-up.

The present invention has been described above as being particularly suitable for use with non-destructive testing of composite materials such as used in aircraft construction. It must be appreciated however that the NDT method and apparatus of the present invention may be used for testing other types of materials where it is suited, and is not limited to testing of composite materials, and is not limited to the testing of aircraft structures.

The present invention is not limited to the use of a pitch/catch probe. Other types of probes may be utilized, such as ultrasonic pulse echo probes, eddy current probes, and others.

It must be recognized that the embodiments described herein are not limited to calculating the mean amplitude data in the frequency range. Alternative methods for combining amplitude data from multiple frequencies may be used such as calculating the average, maximum, minimum, etc.

What is claimed:

1. A system for detecting internal structural defects in a test object, the system comprising:

a probe configured to launch into and receive from the test object acoustical waves, and to produce probe output signals representative of the acoustical waves received from the test object;

an acquisition and computing unit (ACU) coupled to the probe and configured to control the acoustical waves launched into the test object, to receive and process the probe output signals and to produce display output signals which are representative of structural characteristics of the test object;

a display coupled to the ACU for receiving and displaying the display output signals; and a controller associated with the ACU and coupled and responsive to a user interface, which includes manually operable controls, the controller operable with the ACU being configured to produce a plurality of parameters, including at least the parameters b), d) and f) below:

a) an amplitude reference curve representative of a defect-free object at a plurality of frequencies;

b) a phase reference curve representative of the defect-free object at a plurality of frequencies;

c) an amplitude curve representative of a defective object at a plurality of frequencies;

d) a phase curve representative of the defective object at a plurality of frequencies;

e) an amplitude display output representative of the probe output signals obtained for the test object at a selected plurality of frequencies, and produced from the probe output signals which have been normalized to the amplitude reference curve for the defect-free object; and f) a phase display signal output representative of the probe output signals obtained for the test object at a desired plurality of frequencies, and produced from the probe output signals which have been normalized to the phase reference curve for the defect-free object; and a composite amplitude display output as a mean normalized amplitude value over a selected frequency range for each position in a surface scan according to the formula $$A_{comb}(x,y) = \frac{\left( \sum_{f=min}^{max} \frac{A_{raw}(x,y,f)}{A_{ref}(f)} \right)}{Nb_f}$$

Where:

$A_{comb}(x,y)$=Combined amplitude data at a given scan position (x,y)

$A_{raw}(x,y,f)$=Raw Amplitude reading at a given frequency (f) and position (x,y)

$A_{ref}(f)$=Reference amplitude of the response at frequency (f)

$Nb_f$=Total number of test frequencies.

2. The system of claim 1, wherein the system is optimized to detect one or more of disbond type defects, delamination defects and potting type indications.

3. The system of claim 1, wherein the controller is configured to enable an operator to select the frequencies for producing one or both of the amplitude display output and the phase display output for carrying out tests of the test object, based on viewing one or both of the amplitude curve and the phase curve.

4. The system of claim 1, wherein the ACU is configured to produce the amplitude reference curve by normalizing amplitudes of return signals for each frequency relative to amplitude curves of the defect free object.

5. The system of claim 1, wherein the ACU is configured to produce the phase reference curve by compensating the phase responses at multiple frequencies relative to phase measurements of the defect free object.

6. The system of claim 1, wherein the frequencies comprise discrete frequency time-slots.

7. The system of claim 1, wherein the controller is configured to provide a two-dimensional scan display.

8. The system of claim 1, wherein the system is configured to produce the amplitude display output as a composite C-scan which shows both amplitude and phase data by keeping a maximum value for the composite display.

9. The system of claim 1, including producing the composite C-scan display output in a form in which amplitude and phase values are summed.

10. The system of claim 1, wherein the controller is configured to produce, responsive to the user commands, at least three display curve output types, including: a combined amplitude display, a combined phase display, and a composite amplitude and phase display.

11. The system of claim 1, wherein the phase display output is compensated by subtracting phase values from the phase reference curve.

12. The system of claim 1, including optimizing signal to noise ratios and/or scanning speed by selecting or limiting a number of discrete frequency test cycles.

13. The system of claim 1, wherein frequencies for the amplitude and phase display outputs for the defective object are selectable by observing the amplitude curves and the phase curve relative to frequency.

14. The system of claim 1, wherein the probe is a pitch/catch probe.

15. The system of claim 1, wherein the probe is one of an ultrasonic pulse, echo probe and eddy current probe.

16. The system of claim 1, wherein the controller is further operable with the ACU being configured to produce the parameter d).

17. A system for detecting internal structural defects in a test object, the system comprising:

a probe configured to launch into and receive from the test object acoustical waves, and to produce probe output signals representative of the acoustical waves received from the test object;

an acquisition and computing unit (ACU) coupled to the probe and configured to control the acoustical waves launched into the test object, to receive and process the probe output signals and to produce display output signals which are representative of structural characteristics of the test object;

a display coupled to the ACU for receiving and displaying the display output signals; and a controller associated with the ACU and coupled and responsive to a user interface, which includes manually operable controls, the controller operable with the ACU being configured to produce a plurality of parameters, including at least the parameters a), c) and e) below:

a) an amplitude reference curve representative of a defect-free object at a plurality of frequencies;

b) a phase reference curve representative of the defect-free object at a plurality of frequencies;

c) an amplitude curve representative of a defective object at a plurality of frequencies;

d) a phase curve representative of the defective object at a plurality of frequencies;

e) an amplitude display output representative of the probe output signals obtained for the test object at a selected plurality of frequencies, and produced from the probe output signals which have been normalized to the amplitude reference curve for the defect-free object; and f) a phase display signal output representative of the probe output signals obtained for the test object at a desired plurality of frequencies, and produced from the probe output signals which have been normalized to the phase reference curve for the defect-free object; and a composite amplitude display output as a mean normalized amplitude value over a selected frequency range for each position in a surface scan according to the formula $$A_{comb}(x, y) = \frac{\left(\sum_{f=min}^{max} \frac{A_{raw}(x, y, f)}{A_{ref}(f)}\right)}{Nb_f}$$

Where:
$A_{comb}(x,y)$=Combined amplitude data at a given scan position (x,y)
$A_{raw}(x,y,f)$=Raw Amplitude reading at a given frequency (f) and position (x,y)
$A_{ref}(f)$=Reference amplitude of the response at frequency (f)
$Nb_f$=Total number of test frequencies.

18. The system of claim 17, wherein the controller is further operable with the ACU being configured to produce the parameter d).

* * * * *